United States Patent [19]

McRae

[11] Patent Number: Plant 6,003

[45] Date of Patent: Sep. 1, 1987

[54] ASIATIC LILY PLANT NAMED 'TRIBUTE'

[75] Inventor: Edward A. McRae, Boring, Oreg.

[73] Assignee: Melridge Inc., Gresham, Oreg.

[21] Appl. No.: 772,158

[22] Filed: Sep. 3, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; John B. Lungmus

[57] ABSTRACT

A new variety of Asiatic lily plant particularly characterized by its large sized upright flowers having a rich orange-red color tone with virtually no spotting, the flowers being borne in large raceme clusters with blooms of excellent form and long persistence both on the plant and as cut flowers. The plant is highly resistant to disease and shows high resistance of virus, it is an excellent garden plant, and its bulbs may be precooled and forced for cut flower production throughout the year. The clone is very vigorous and is a good grower and propagator.

1 Drawing Figure

BACKGROUND OF THE NEW PLANT

This new variety of lily plant originated as a seedling selected from a group of seedlings resulting from my crossing of the clonal cultivar "Sunstar" (unpatented) and the cultivar "Connecticut King" (unpatented) at Sandy, Oreg., in the course of breeding efforts carried on by me since 1975 with the object of developing flowered, unspotted, upright Asiatic lilies in both orange and orange-red color tones suited to out-of-season forcing, these features being heretofore unknown in the lily breeding art. This new variety of lily plant has been asexually reproduced by me and under my direction at Sandy, Oreg., and successive generations produced by bulb scale propagation and natural propagation from bulblets have demonstrated that the novel and distinctive characteristics of this new variety are fixed and hold true, under asexual propagation, from generation to generation.

This new plant has been found to be vigorous and a good grower and propagator, as observed at Sandy, Oreg., and in addition this plant possesses to a high degree the desirable characteristics of hybrid vigor, great hardiness, and disease resistance, possessing all of the desired characteristics of excellence of form, color, and habit. This plant has also been found to be well suited for forcing out of season when bulbs are properly precooled. October-dug bulbs, properly precooled and potted in January, will flower under glass, at moderate temperatures and without supplementary lighting, in an average of 75 to 80 days in western Oregon.

DESCRIPTION OF THE DRAWING

This new variety of lily plant is illustrated by the accompanying photographic drawing, which shows the open bloom together with foliage and buds and illustrates the flower form and the tepal arrangement, the flower being hand-painted to show the true and distinctive orange-red color tones as herein specified.

DESCRIPTION OF THE NEW VARIETY

The following is a detailed description of my new variety of Asiatic hybrid lily, with nomenclature according to The International Lily Register of The Royal Horticultural Society of London, England, Second Edition; and the color designations are according to The Royal Horticultural Society's Colour Chart published in 1966.

THE PLANT

Origin: Seedling.

Parentage:

*Seed parent.*—Lilium "Sunstar" (unpatented).

*Pollen parent.*—Lilium "Connecticut King" (unpatented).

Classification:

*Horticultural.*—Division I-A, Upright Asiatic lily hybrid, of the Horticultural Classification of Lilies by The Royal Horticultural Society of London, England.

*Commercial.*—Asiatic hybrid lily cultivar.

Form: Erect and stately single stem.

Height: About 90 to 100 cm. from bulbs of about 15 to 18 cm. in circumference, provided light levels are adequate. (Low light levels cause "stretching").

Growth: Vigorous and upright.

Foliage:

*Quantity.*—Abundant.

*Leaf size.*—About 8 to 12 cm. long and about 1 cm. wide.

*Leaf shape.*—Lanceolate.

*Texture.*—Leathery.

*Aspect.*—Glossy.

*Color.*—Both upper and under sides, medium green to dark green.

Bulbs:

*Size.*—Varying, ranging to 25 cm. in circumference.

*Color.*—White.

THE BUD

Form: Obtuse and long ovoid.

Size: About 8 to 9 cm. long and about 5 to 6 cm. in circumference just prior to opening.

Opening rate: The bud opens slowly.

Color: Orange-red, R.H.S. 34-D, just prior to opening and as the tepals begin to unfurl.

Peduncle:

*Length.*—About 6 to 8 cm.

*Character.*—Erect.

*Color.*—Dark green with reddish-purple overlay.

THE FLOWER

Blooming habit: Annually in mid-season, flowering once and profusely.

Size of flower: Large, about 15 to 18 cm. in diameter with outer tepals about 2 cm. wide and inner tepals about 3 cm. wide.

Borne: As a raceme of about 9 to 11 blossoms on a single stem originating from a bulb about 18 cm. in circumference.

Shape: Flattened cup-shape with broad tepals having lightly fluted margins.

Tepalage:

*Number.*—Six.

*Arrangement.*—Imbricated.

*Aspect.*—The flower is shiny.

*Color.*—The flowers are distinguished by their deep orange-red color tone, R.H.S. 33-B, at the tepal tips and margins, shading to slightly lighter R.H.S. 30-A/B in the center of the tepals. The nectaries are covered with very short white pubescence, and there is a lighter area of R.H.S. 30-C about 1 cm. long and about 0.5 cm. wide just above the nectaries. The tepals have lightly ruffled margins.

*Spotting.*—Occasionally 2 or 3 tiny, inconspicuous pigmented papillae appear on a flower, parallel to the nectary furrows in the flower center. These maculae are scarcely noticeable.

Color change: As the flower ages, the color becomes slightly deeper in the center of the flower, but this is a subtle change.

Pedicel:

*Length.*—About 10 to 15 cm., ascending at a 45° angle from the stem axis.

*Form.*—Sturdy with no secondary buds.

*Color.*—Medium to dark green with medium reddish-plum overlay.

Fragrance: None.

Lasting quality: The flower is long lasting, both on the plant and as a cut flower.

Disease resistance: The flower and plant are resistant to disease and in particular they are resistant to Fusarium bulb rot and Botrytis blight as observed in western Oregon.

THE REPRODUCTIVE ORGANS

Stamens:

*Arrangement.*—Typical of genus Lilium.

*Number.*—Six.

Filaments:

*Length.*—About 5 cm.

*Color.*—Light orange-red, R.H.S. 33-C.

Pollen and anthers (dehisced):

*Color.*—Orange, R.H.S. 28-B.

Pistils: One in number, about 5 cm. long.

Stigma:

*Color.*—Grayed red, R.H.S. 180-C.

Characteristics of ovary: Typical of genus Lilium.

THE FRUIT

Fertility: The fruit is fertile.

Shape: Ovoid.

Color at maturity: Soft brown, sometimes overlaid with soft plum.

This new variety of Asiatic hybrid lily most nearly resembles 'Matchless' (U.S. Plant Pat. No. 4,879) but the new variety has larger flowers with broader tepals, improved flower form, thicker flowers, and lightly ruffled tepal margins.

I claim:

1. The new and distinctive variety of Asiatic hybrid lily plant, substantially as herein shown and described, characterized in particular by the orange-red coloration of its large sized, virtually unspotted flowers, by its high tolerance of virus, its vigorous growth and rapid natural propagation, the excellence of its flower form, and its versatility both as a garden plant and as a cut flower producer from precooled bulbs forced out-of-season under glass.

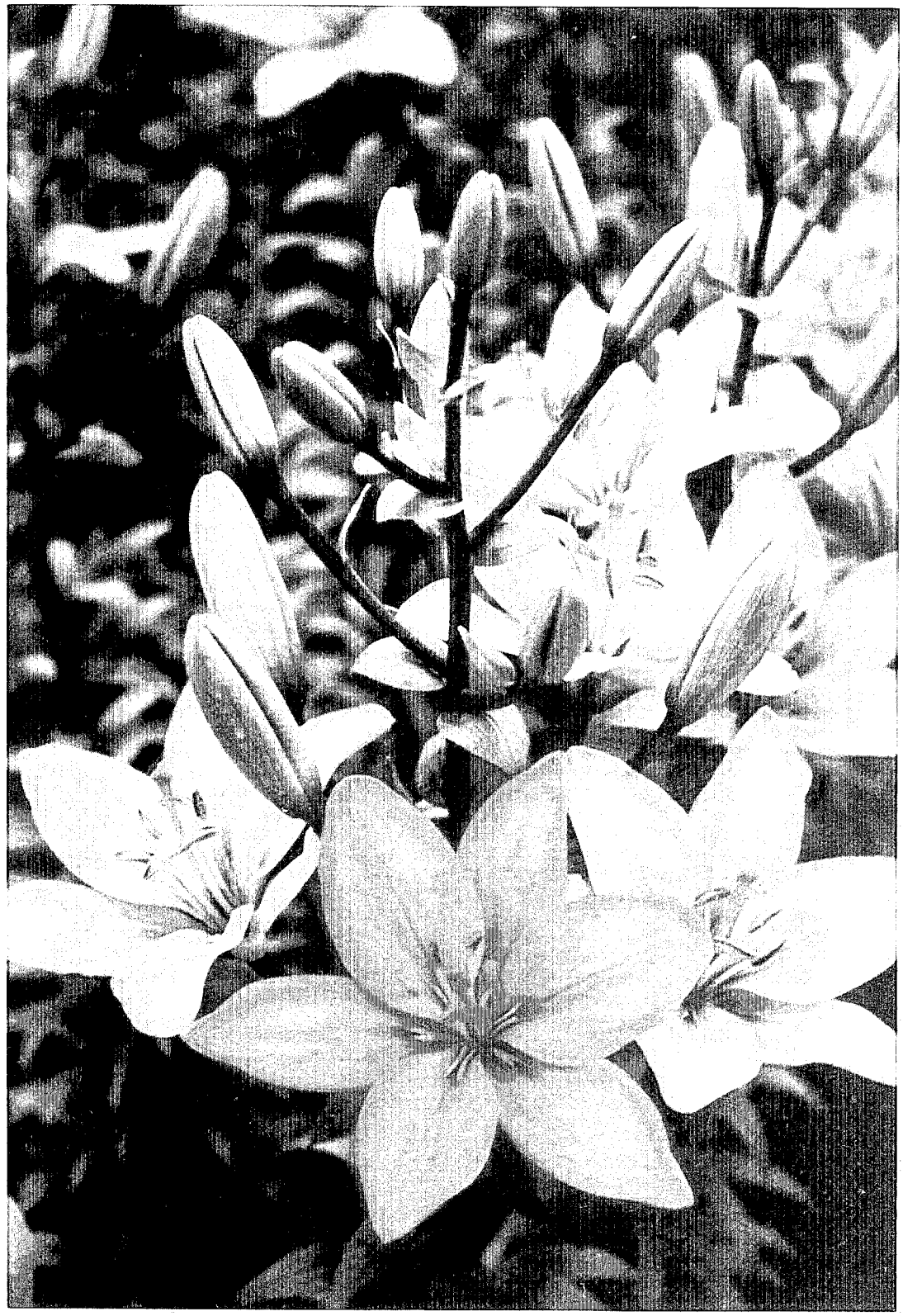

* * * * *